United States Patent [19]

Kiyasu

[11] 4,338,396

[45] Jul. 6, 1982

[54] HEART ATTACK SCREENING METHOD AND PROCESS

[76] Inventor: John Y. Kiyasu, 94 Meadow St., Garden City, N.Y. 11530

[21] Appl. No.: 177,662

[22] Filed: Aug. 13, 1980

Related U.S. Application Data

[63] Continuation-in-part of Ser. No. 922,885, Jul. 10, 1978, abandoned, which is a continuation-in-part of Ser. No. 730,102, Oct. 6, 1976, Pat. No. 4,105,499.

[51] Int. Cl.³ .................... C12Q 1/50; B01D 15/08
[52] U.S. Cl. ....................... 435/17; 210/635; 210/927; 435/194; 435/803; 435/815; 435/816
[58] Field of Search ............... 435/17, 194, 803, 816, 435/815; 23/230 B; 210/198.2, 635, 656, 927

[56] References Cited

U.S. PATENT DOCUMENTS

| | | | |
|---|---|---|---|
| 3,179,587 | 4/1965 | Battista et al. | 210/198.2 |
| 4,013,513 | 3/1977 | Lederer | 435/815 |
| 4,046,634 | 9/1977 | Mercer | 23/230 B |
| 4,056,485 | 11/1977 | Adolf et al. | 23/230 B |
| 4,125,492 | 11/1978 | Cuatrecasis | 210/635 X |
| 4,166,766 | 9/1979 | Metzenberg et al. | 435/815 |

*Primary Examiner*—John Adee
*Attorney, Agent, or Firm*—E. Janet Berry

[57] ABSTRACT

Improved steps and methods for rapid, efficient and accurate assay of the CPK isozyme MB (cardiac fraction) and other determinations using chromatographic column technique. The improvements are especially adapted for carrying out rapid diagnostic tests in clinics and hospitals. Also contemplated improved apparatus and methods and uses of same adapted for the test method, such apparatus having novel features which can be packaged and merchandised in kit form. Other special features include use of electrophoresis either with or without the conventional chromatographic column analyses and using a selected colored (preferred-green) marker dye. Another special feature is that the used columns of the improved design can be conveniently recycled using the same solutions.

5 Claims, No Drawings

HEART ATTACK SCREENING METHOD AND PROCESS

This application is a continuation-in-part application of copending patent application Ser. No. 922,885, now abandoned, filed July 10, 1978 which in turn is a continuation-in-part application by copending patent application Ser. No. 730,102, filed Oct. 6, 1976, now U.S. Pat. No. 4,105,499.

The invention consists generally of improved apparatus and a kit packaged improved methods and apparatus for isolating, identifying, and quantitatively measuring the MB iso-enzyme of creatine phosphokinases in fresh human blood serum and making other quantitative and qualitative blood and blood serum tests.

It has been known and practiced in the past to make a quantitative separation of the three iso-enzymes of creatine phosphokinases (CPK) by either electrophoresis of anion-exchange chromatography. They are separated into three separate entities: CPK-MM, MB, and BB. The MB fraction of creatine phosphokinases has generally been expressed as a percentage of the total CPK in human serum. The determination and finding of CPK-MB in human serum is almost completely indicative of the condition called myocardial infarct, otherwise and commonly known as a "heart attack" in the patient.

The column separation of the three iso-enzymes of creatine phosphokinases (CPK)—by anion-exchange chromatography for routine clinical laboratory use—has been found to have a number of difficulties which include the following:

1. High speed columns made of DEA-glass beads although effective in isolating the cardiac fraction (MB) are quite expensive for routine testing. Therefore a 1.5 ml. column which is generally not considered regenerable (re-usable) becomes a considerable cost disadvantage.
2. Columns made of DEAE-dextran (polyglucose polymer glucose) effective for the process except that the flow rate is slow, and furthermore they are compressible such that hand pressure using hand bulbs, for example, result in compaction and further slowing of the flowrate.

It has been found that by using columns of several commercially available anion-exchangers such as DEAE-dextran or DEA-glass beads together with certain elution buffers, the CPK-MB can be isolated predictably, reproducibly and proportionately. The fractions are isolated in a form sufficiently concentrated that the CPK-MB activity may be determined on this eluate thereby proving clinical data completely consistent with the condition termed myocardial infarct and the results indicate suggested degrees of infarct size (severity of the "heart attack"). The simplicity of the invention procedure is such that different technologists can obtain essentially identical results on a given blood serum specimen.

In general, the invention includes the following features:

1. The isolation procedure, including the order of elution buffers with emphasis on a "priming" step before introduction of the MB fraction. A method for preparing a suitable laboratory control for CPK-MB is also included as a necessity.
2. A hybrid column, having both high speed (through-put rate) and low cost of matrices.
3. A non-cloggable spigot plug to replace others which are usually of the fritted plastic or glass disc type. The material preferred is a 5 mm. slug of a filter tip as used in conventional filter type cigarettes.
4. New column matrices in which a 30 mm. × 10 mm. slug of DEAE-cellulose "filter tip" comprises, if desired, the entire internal core of a CPK column.
5. The design and chassis of the CPK column, with description of suitable racks for use in conjunction with said columns in a clinical laboratory.

Using a combination of DEAE-dextran and DEA-glass beads, a completely satisfactory column can be made requiring only 0.25 ml. of DEA-glass beads. A similar high density matrix such as inert glass beads or reagent grade sea sand can be used in place of the DEA-glass beads.

DEAE-dextran is a high capacity anion exchange dextran polymer of relatively low density. DEA-glass beads, sea sand, or inert glass beads are high density non-compressible matrices. A hybrid column made of low density dextran and one of the indicated non-compressible materials in a suitable buffer behaves very predictably for the test. Upon inversion of the column by a simple hand rotation the sand or beads consistently layers to the bottom of the column effectively shielding the porous retainer of the column. Since the DEAE-dextran is layered on the upper most portion of the column bed, the flow rate can readily be speeded by the application of the hand bulb. If the column is found to be very slow this defect is readily correctable by the application of suction or partial vacuum on tope of the column by the same hand bulb. The back suction applied to such a column serves to lift the bed matrices off the porous column retainers thus freeing small dextran particles from the retainer. Upon compression of the bed with the same hand bulb, the more dense sand or beads settles first and serves as a non-compressible "porous" barrier thereby preventing clogging, channeling and other undesirable effects in the column.

There are special advantages in using columns of certain design, size, and type. In addition to the fact that the columns should be of a convenient and easily usable size, both in length and diameter, it is also important that these columns be readily transportable by conventional carriers, readily stackable in package form thus occupying minimal bulk storage space, and readily inspected for any matrix defects (air bubbles, bacteria, and the like).

Each column has the same bed capacity so that the elution protocol will result in reproducible recovery of the CPK-MB fraction. In addition, for routine clinical laboratory analysis, a 1.5 ml. aliquot of serum is a highly useful aliquot since conventional sample cups used in autoanalyzers for serum, and other samples are in fact designed for 1.5 ml. samples. Thus, the bed capacity of the column, the elution characteristics, and the like should be designed around this load capacity as closely as possible.

The column matrix for use within the selected columns should be of such size and material that high flow rates are maintained to give both speed in performing the test as well as accurate and reproducible results. For adoption as a practical clinical tool, the matrix should also and preferably be composed of readily available materials of relatively low cost.

A diethylaminoethane derivative of dextran suitably cross-linked and commercially available (i.e., Pharmacia-Sephadex A-50, etc.) is prepared by hydrating directly into Solution #1 (0.1 M NaCl, 0.05 M "Tris", 0.1% sodium azide, 0.016 M dithiothreitol, pH 7.9). This slurry is made by gentle stirring with sufficient buffer so that upon settling of the anion exchanger an equal volume of supernatant liquid is available to the bed volume. This swelling and hydration step is allowed to age at least several days at 4° C. before the suspension is used for pipetting into empty columns. After the aging period, the anion-exchanger suspension is brought to room temperature and approximately 5 ml of the hand-stirred slurry is pipetted into each column. The approximate volume of the resin should be 2.5 ml per column. This bed volume-when compacted, however, by buffer flow through the column, or by hand bulb pressure, effectively becomes a 2.0 ml bed volume.

The above column may be fitted with a sintered disc or fritted disc or a 5 mm. cigarette filter tip. The column flow matrices may be improved by the addition to this column of 0.25 ml. or reagent grade sea sand, inert glass beads (such as "Super Brite" beads, etc.) or DEA-glass beads (Corning).

The procedure of isolating a slug of the CPK-MB fraction is based on the use of only two eluting buffers, i.e. herein identified as Solution #1 and Solution #2. The composition of the above are the following.

Sol. #1 0.05 M "Tris", pH 7.9, 0.1 M NaCl, 0.016 M DTT and 0.1% sodium azide.
Sol. #2 0.05 M "Tris"; pH 6.9, 0.3 M NaCl, 0.016 M DDT and 0.1% sodium azide.

The elution with Solution #1 quantitatively removes all of the CPK-MM fraction, resulting in absolutely no carry over into the MB slug. The prime step, in fact, assures this (1 ml of Solution #2). Upon changing to a clean collection tube—the "peak slug" of the CPK-MB fraction is obtained—by eluting the column with 2.0 ml of Solution #2. The purpose of this is two-fold as follows:

1. An MB fraction devoid of MM carry over.
2. An MB fraction of sufficiently high concentration.

By fulfilling the two above conditions, both selectivity and sensitivity are obtained. Under the conditions of the test, the "2 ml" Solution #2 eluate may be examined either by electrophoresis or by simply assaying for CPK activity using the so-called Rosalki substrate. A typical prescribed procedure is ideally suited for the Beckman TR Enzyme Analyzer, the Dupont ACA, or performed manually on the Gilford 300-N, or using any other suitable instrumentation. The overall procedure should not take more than one-half hour, including spinning down the clotted blood and will require a minimum of 15 minutes for a total turn-around time.

The procedure is sufficiently sensitive to detect a myocardial infarct one half hour after onset—on a total CPK serum activity of 200 mIu/ml. This means that the procedure is sufficiently sensitive to be used as an admission index in an emergency room or special care service.

The clear glass columns are readily inspected for entrapment of air bubbles or any other irregularities. Air bubbles are easily removed by gently inverting the columns several times. The procedure is as follows:

Step 1. Remove the top cap first, then remove the spigot nipple. Allow the supernatant liquid to drain through by gravity.
Step 2. Assay patient serum for total CPK. If the activity is greater than 200 mIu/ml, proceed as below. Otherwise request another patient specimen—if so desired.
Step 3. Transfer 1.5 ml of patient serum into the column bed. Allow serum to drain through bed by gravity.
Step 4. Wash column with 2 or 3 aliquots of 4–5 ml of Solution #1. Three aliquots are recommended when the total CPK is greater than 1000 mIu/ml.
Step 5. Prime the column with exactly 1.0 ml. of Solution #2.
Step 6. Change collection to a clean test tube.
Step 7. Elute column with exactly 2.0 ml of Solution #2 and assay this eluate for CPK activity.

Since the eluate of Step 7 above represents the MB fraction—this CPK activity is expressed as an absolute value.

An MB signal of 4 mIu/ml is considered negative, 5 mIu/ml is considered questionable. Anything greater than 5 mIu/ml is considered positive for myocardial infarct.

If the technologist or any other personnel is in doubt with the result, the assay or the MB fraction can be repeated. If the doubt is still not resolved, another aliquot of the same serum should be processed through the same column procedure on another, unused, column. The ultimate degree of doubt should result in drawing another blood specimen, that is, from the same patient. In the acute phase of myocardial infarct—the CPK-MB signal will not only remain—it will tend to get higher and peak dramatically at approximately 12 hours after the heart attack. The MB signal generally is no longer detectable 48 hours after the myocardial infarct.

Proper quality control requires that all technologists on different shifts, day or otherwise compare results based on processing the same specimen. If Solution #2 is used instead of Solution #1, for example, completely erroneous results will occur. This Solution #1 is color coded for instance green and Solution #2 (a smaller bottle) is color coded for instance orange. The use of food coloring (green) may be dissolved in the Solution #1 to further prevent cross contamination of each respective solution. The recommended dosage is 1 drop of green to 1 liter of Solution #1. Pipettes may also be so color coded with colored tapes—in order to avoid cross contamination, and if this is done the same pipette may be used over and over again. These solutions and columns are "preserved" by the use of 0.1% sodium azide and have been used, opened, closed, repeatedly at room temperature (20° C.–30° C.) for longer periods of time with no deleterious effects. However, if any sediments, opaque clusters or the like which may be suggestive of microbial growth, is evident the solution or column must be discarded. Frequent checking the buffers for proper pH is recommended.

The use of rubber hand bulbs are highly recommended not only for pipetting serum solutions, but also for applying pressure or suction to the column during Step 4 when the MM fraction of CPK is being washed out. The efficacy at Step 4 is only for speed and the hand bulb technique can be omitted if time is of no urgency. It is highly recommended that these columns be discarded after use, or recycled only in accord with a give procedure as a precaution against hepatitis, and other undesirable results. These columns have been designed not only for accuracy, precision (reliability) but also with regard for cost. Thus, they provide high quality analytical results but are truly disposable.

Experiments designed for defining the elution characteristics, separation, recovery, and other details reveal the following:

1. Upon the addition of 1.5 ml. of fresh human serum onto this column, and after wash out with two (4–5 ml) aliquots of Solution #1, 100 percent of the MM fraction is removed from the column. A third aliquot of Solution #1 simply assures the absoluteness of this wash out procedure.

2. The "priming" step of 1 ml of Solution #2 begins to bring out the fore-shoulder of the MB fraction and has a low MB signal.

3. The final collection elution of 2 ml of Solution #2, brings out the slug of MB peak with a good signal for CPK measurement. The use of green (food color) in Solution #1 results in the elution of the green pigment with Solution #2 in this same MB fraction, and is therefore a desirable visual marker for the MB fraction. This green pigment in no way interferes with the CPK-MB assay when using the Rosalki procedure.

4. This MB fraction constitutes approximately 70 percent of the total MB fraction with considerable consistency since both shoulders of the peak are involved.

5. Up to 10 percent of the BB fraction may be recovered in the MB fraction, but this does not cause any diagnostic problems since the absolute BB signal is quite low in adult human serum even in subjects suffering from renal impairment.

Controls:

In addition to inter-technologists performance controls as above described, it is recommended that a known CPK standard of established isoenzyme composition such as is used in electrophoresis be used daily for column analysis. Instead of adding 0.5 ml or 1.0 ml of distilled water as in the direction for electrophoresis analysis, such standards may be reconstituted in 16 ml of 0.01 M phosphate buffer of pH 7.4 to which is added 7 drops of 10 percent DTT (dithiothreitol). This solution is stored in the refrigerator overnight in order to assure the re-activation of inactivated BB and MB. The mixture is then generally stable for 10 working days allowing ten 1.5 ml aliquots for use as column analysis controls.

The second and most important control is performed by electrophoretic analysis of the column MB fraction. A MB signal of 20 Iu/ml can be readily analyzed by agarose-Rosalki-fluorometric analysis if 4–5 ul of specimen is applied on the gel or if the entire MB eluate is concentrated (i.e. Amicon, or similar concentrator) approximately ten fold, and applied conventionally with a micro-applicator.

It is important to note that CPK-MB and BB is readily oxidized when admixed with other disulfide containing proteins, and has caused considerable controversy among different laboratories and investigators.

Therfore, it is important to emphasize the need to use highly recommended CPK isoenzyme standards (i.e. Helena Labs, etc.) and furthermore to recognize that such standards, even when obtained from the same manufacturer may show lot-to-lot variability.

Reagents

Columns—These columns are designed for clarity (visual observation), flow and wash out design, quality control especially as related to uniform bed volume, and disposability. The diethyl-amino-ethyl dextran is thoroughly hydrated, aged and stabilized with a bacteriostatic preservative. The column is already equilibrated in buffer #1 and is ready to be used in a stand-by mode. In the event a particular column is drained but not actually used, the addition of buffer Solution #1 and the re-capping of the column, results in the original storage form.

Buffers

Solution #1 and Solution #2 are packaged in a 10 fold concentrated form. Each 20 ml vial must therefore be diluted with 180 ml of deionized or distilled water. Appropriate color coded labels are inserted for use in properly labelling the working solutions.

*Unopened packages may be stored in the refrigerator (0°–4° C.), however, opened kits should be kept at room temperature.

Stability

Columns and kits packaged for the method may be stored at 0°–4° C. for a period of one year and opened packages at room temperature for a period of three months.

Specimen collection

Clotted blood samples obtained in venipuncture collection tubes are adequate. Hemolysis does affect the total CPK activity (increase) when assayed using the Rosalki substrate but does not at all affect the MB fraction. Serum should be left on the clot and refrigerated wherever possible. The glutathione reductase of red blood cells presumably maintains a redox environment suitable for MB stability. Serum separated from the clot should be assayed within 4 hrs. when kept at room temperature. It is believed important to keep the serum on the clot and refrigerated, if the MB assay is not immediately performed. Wherever at all possible the use of fresh human serum is recommended.

Procedure

CPK assay

The use of the Rosalki procedure is recommended in view of its sensitivity and reliability. Myokinase, when present, will give a false high total CPK. However, myokinase is not at all recovered in the MB fraction and therefore does not interfere with the signal. Also recommended is the use of instrumentation at 37° C. employing zero-order kinetics, whether manual or automated. This recommendation is made because of the fact that different specimens have different degrees of lag phase, therefore, fixed point readings may create artifacts and values based primarily on differences of lag phase.

CPK as an Enzyme

This enzyme is a dimer, with no catalytic activity when it is present as a monomer and/or in the disulfide form. The BB and MB fractions are more readily oxidized than the MM isozyme although all can eventually be oxidized and therefore inactivated. Since sera and tissue extracts have many disulfide proteins (albumins, globulins, and the like), it is understandable that different investigators and different laboratories have produced much conflicting reports. Extreme caution must be observed because of the sulfhydryl-disulfide interchange and judicious handling of sera and controls must be employed. CPK Standards generally used for electrophoresis are probably the best controls. Such "protein-free" controls may be "spiked" with fresh human serum for column procedure control. Sera from pregnant females are found generally low in total CPK activity but any other fresh serum of low CPK activity must be used as a suitable base.

These columns are extremely efficient and perform equally well with low or "normal" protein concentration. However, it is recommended that column controls should mimic as closely as possible the unknowns (fresh human sera).

Rack

The test rack when designed to occupy minimal bench space, as well as to provide clarity, specimen indentity and minimal cross contamination. Therefore the column spigots are "free-hanging", sufficiently high to prevent back-splashing, and yet generally with a low center of gravity. The collection supports actually may serve as a sample tray again facilitating specimen identification. The plastic sheets are laminated wherever possible for structural support and should be cleaned only with cold tap water either under the sink faucet or using a clean wet cotton gauze. The rack should be cleaned once a day in order to minimize sera contamination and for general hygienic purposes. This rack is quite expensive and should be so handled as valuable property.

Note: two holes are reserved for pipette Solution #1 and Solution #2. These pipettes should be color taped so that they will only be used with their respective bottles. Mouth pipetting should be discouraged wherever possible. Disposable 5 ml Mohr pipettes with a cotton plug are recommended for routine use. The receptacles are so designed to house them. Solution #1 and Solution #2 may be substituted by other salts such as potassium chloride, sodium bromide, potassium bromide and the like of equivalent ionic strength. The optimum molar concentrations of these salts may vary depending on their effective ionic strength. The particular salts and buffers employed in the Examples are selected for convenience as they are routine laboratory reagents.

The materials do not generally require any special handling as they are also selected to avoid fragmentation and/or friability. However, they should be handled with such care so as to avoid causing excess bubble entrapment into the column matrices. Such entrapments are readily removed by repetitive inversion of the column.

The spigot is a further important portion of the column and it has been discovered that a 5 mm. plug made from the filter tip of a commercial cigarette can be used quite satisfactorily for this purpose. These filter tips are generally made from linearly milled cellulose fiber of controlled porosity designed for prescribed flow characteristics (for instance inhalation). Cigarette filter tips from all brand name cigarettes tested thus far have been found to be perfectly suitable.

Thus one embodiment of the invention and one which is especially adaptable for packaging, storage and distribution in kit form is made from DEAE-dextran, sea sand (reagent grade) and the commercial cigarette filter tip employed in combination. Such an assembled device has been found to provide both fast flow and also high analytical accuracy and reproducibility when used in CPK-MB determinations in fresh human serum.

Analytical columns, especially in the clinical service environment, are generally not considered re-usable. In the case of anion-exchange columns, a number of matrices after repeated use, begin to disintegrate physically and also, to some extent, co-valently. Their selectivity changes slightly, but sufficiently to alter elution patterns with diminished separation of component fractions.

The DEAE-dextran is perfectly stable when treated with Solution #1 or #2 and fresh human serum—such that these columns can be used repetitively through the procedure. In fact, careful elution of a fresh human serum containing known composition of the three CPK isozymes (MM, MB, and BB), repetitively, on the same day or on subsequent days results in the same elution patterns and with consistent and satisfactory MB resolution.

The above advantages make routine applications even simpler in that re-usable columns can be used in physicians offices in dip-stick fashion, and in technique-free procedures in busy automated clinical laboratories. The number of repetitive runs on one column has not been exhaustively evaluated but it does appear that at least ten (10) consecutive runs can be made on a column or cartridge before discard is necessary, thus reducing cost, and providing other advantages. It is also necessary in repetitive (recycle) use that the samples processed, in re-usable columns, be non-hemolyzed, clear and free of jaundice (as a matter of precaution).

Steps in Regeneration of a column:
1. after a MB run, pass through 10 cc. of additional Solution #2.
2. for optimal equilibration, pass through 5 cc. of Solution #1.
3. The DEAE-dextran column is as good as and equivalent to its original condition.

The invention will further be described and illustrated by the following specific examples. However, it is in no way intended to limit the scope and parameters of the invention thereto.

EXAMPLE 1

In carrying out the procedure of the invention, a commercially available DEAE-dextran columns from E-C apparatus or a prototype column such as obtained from Hofmann LaRoche may be used with attached and modified elution buffers. A bed volume of 1.5 ml. of DEA-glass beads is used and the beads must be individually poured into the column. Glass or dextran (2 ml bed capacity) columns are equilibrated in 0.1 M NaCl (sodium chloride) containing 0.05 M "Tris" buffer of approximately pH 7.9. More particularly, the top cap of the column is first removed followed by removal of the bottom spigot. The excess buffer is there removed by gravity flow or, if desired, from the supernatant liquid using a Pasteur or similar pipette. If the freshly obtained human serum has a total CPK activity of 200 Iu/liter or greater, 1.5 ml. of this serum is transferred onto a column prepared as described above. When the serum has completely passed through the column bed, the column is washed with two or three aliquots of a first solution (0.1 M NaCl, 0.05 M "Tris" pH 7.9) using about 4-5 ml. per aliquot. The column is then primed with 1 ml. of a second solution (0.3 M NaCl, 0.05 M "Tris", pH 6.9). The MB fraction is then collected in a clean test tube by washing the column with the following indicated aliquot of the second solution 2 ml. for DEAE-dextran column, and 1 ml. for the DEA-glass bead column. The eluate obtained is assayed for CPK-MB.

If this fraction is found to have a CPK activity of 5 or less (Iu/liter), the specimen is considered negative for infarct.

A CPK activity greater than 5 (Iu/liter) is considered positive for infarct, that is, provided all the clinical symptoms in the patient are consistent with a myocardial infarct conditon.

A suitable control for the above procedure is carried out by using the CPK-isoenzyme standard prepared conventionally for electrophoretic analyses. Such as appropriate control is the Helena Laboratory CPK-isoenzyme standard. One vial of this preparation is diluted with 16 ml. of 0.01 M phosphate buffer, pH 7.4, to which is added seven (7) drops of 10 percent DTT (dithreitol). Such a control prepared as above described can generally be used for a period of two weeks if it is stored in the refrigerator. It should be put through the entire analytical procedure to establish that the overall process is working predictably and reproducibly before its use on patient serum.

EXAMPLE 2

The formulations of the following bed matrices are designed for the processing of 1.5 ml. of fresh human serum and are comparable in use to the 1.5 ml. bed volume column made of DEA-glass beads or the 2.0 ml. bed volume column made of DEAE-dextran as described above in Example 1.

The DEAE/DEA bed: 0.75 ml. DEAE-dextran /0.25 ml.

DEA-glass beads mixed and hydrated in a suitable buffer.

The DEAE/Sand bed: 0.75 ml. DEAE-dextran /0.75 ml of reagent grade sea sand or inert glass beads and hydrated in suitable buffer.

Commercially available DEAE-dextran columns from E-C Apparatus or commercial proto-type column can be made "fast" by adding dry glass beads or sand to the existing hydrated columns. The proportion and volume of the hybrid columns described above are designed to replace the mono-bed columns of either DEAE-dextran or DEAE-glass beads, suitable for processing 1.5 ml. of human serum.

In Example 1 above columns made of hybrid matrices were described for the purpose of achieving high flow rates and low cost material matrices using a combination of DEAE-dextran and reagent grade sea sand or inert glass beads. The other important part of a column is the spigot or retainer which retains the column bed or matrices but without unduly slowing the flow rate.

Conventional columns have, as a retaining septum, either a plug of glass wool, a fritted or sintered glass or a plastic disc or plug. Ordinary cigarette filters such as those attached to the cigarette bodies of commercial brand filtered cigarettes function quite well as disposable plugs and are usable in conjunction with both the hybrid Dextran-Sand columns and the Dextran-Glass Bead columns. The fritted retainers of commercially available columns from E-C Apparatus or a commercial proto-type column are removed and replaced with a 5 mm. plug of the filtered tip of a commercial brand filter cigarette. The plug of the filter tip is then inserted into the spigot receptacle and is covered with 0.5 ml. of sea sand or glass beads. A hydrated 0.75 ml. aliquot of DEAE-dextran in an appropriate buffer is then delivered to the column and a cap is placed on both top and bottom of the column. After repeated inversion, and after all trapped air bubbles have been removed the sand or glass beads is layered directly above the filter plug and finally layered by the DEAE-dextran. Such a column design shows extraordinary flow rates and behaves well even with compression or decompression.

The cigarette filter plugs presumably work better than fritted or sintered discs in that they provide a linear flow (parallel channels of the fiber matrix), and also serve as a slightly elastic cushion allowing the total column matrices to respond to hand bulb compression or decompression. A further advantage for the use of cigarette filter plugs is that the unit cost per column part becomes quite minimal and thus allowing for the design of a truly disposable analytical column. Finally, a linear filter plug, as provided in the filters of filtered cigarettes have sufficient structure so as not to collapse, or plug up and thus result in higher flow rates. Thus a 0.75 ml. DEAE-dextran/0.5 ml. sea sand or glass bead/5mm. linear filter plug hybrid column has been designed for high speed analytical work especially suitable for the STAT determination of CPK-MB in fresh human serum.

EXAMPLE 3

In clinical laboratory work two sizes of test tubes are commonly available and used, i.e. 16 mm×100 mm. or 13 mm.×100 mm. These sizes are the same as the Vacutainers or the containers used for blood collection which are regularly of these two sizes. It is therefore convenient to design a column chassis, which incorporates these two sizes. Since the 13 mm. (O.D.) tube fits very nicely into the 16 mm. (O.D.) tube, a column chassis can easily incorporate these two diameters. The incorporation of these two sizes also provides a number of functional advantages as will be more apparent in the following detailed description.

The upper portion of the column chassis has an outer diameter of 16 mm. and is 50 mm. in height. Continuous to this upper portion the bottom portion of the column chassis will be 13 mm. in outer diameter and 30 mm. in length. The inner diameter of this lower portion will be 10 mm. The shoulder provided by joining the 16 mm. to the 13 mm. cylinders will provide two functions:

1. The shoulder provides a means by which the column will seat firmly in the holes provided in a rack or in the absence of a rack, and allows this column to sit directly into a receiving 16×100 or 16×150 test tube.
2. The lower (10 mm I.D.) portion of the comumn will serve as the receptacle for the column matrices whereas the upper portion of the column (16×50) will serve as a reservoir for the eluting buffer.

Another ancillary function of this column chassis design is the fact that this conformation allows the stacking of empty columns one into the other thus simplifying and making compact packages suitable for mailing and storage. Finally, the meniscus of the 16/13 junction will serve as a useful marker of bed volume size, both for the manufacturer and the user, in terms of quality control, since the elution pattern of a column is a function of elution volume and also matrix bed size (volume).

Finally, this special column design allows the spigot of the column to "hang-free" especially when used in a rack assembly since the 16/13 junction will secure the column suspension.

The spigot design is shown with both an inner and outer spigot design. The spigot with shoulders for outer surface of the 13 mm. clylinder allows for "unobstructed" interior flow. The spigot with shoulders designed for the interior walls of the 13 mm. cylinder has the following desirability:

1. The column design is more visually attractive and also minimizes obstruction when it is inserted into the holes of a rack or into a 16×100 or 16×150 recipient tube.
2. The interior spigot has a receptacle for a 5 mm. filter plug, as well as a 0.5 ml. aliquot of sea sand or inert glass beads. This means receptacle can be used to house a portion of DEAE-filter tip cartridge, if desired.

A suitable rack design preferably has one row of holes. The rack hangs rather low thus preventing the need for a wide base (center of gravity), and occupies minimal bench space. The ⅛" plexi-glass or otherwise transparent plastic is essentially three separate linear pieces shaped into a C-shape on its side with the back of the C serving as the horizontal platform. This design allows the three pieces to be laminated easily either with a suitable glue, or glue may be used with screw nuts or by plastic "welding plugs". The laminated legs provide firm vertical support while the horizontal table will retain some flexibility. The removable and inversible tube block serves two purposes:
1. It helps to stabilize the rack structurally and reinforces a lower center of gravity.
2. It can be removed, inverted and laid on top of the collector tray of the rack. The 14 mm. holes then serve as a receptacle for the 2 ml. sample cups used for collecting 1 ml. of the MB fraction. During such collection, the different specimens processed can be transported in the tube block to the analyses area.

EXAMPLE 4

It is also possible to unplug the filter tip commonly used on many brands of filtered cigarettes or some facsimile thereof employed as the entire column matrices for the column separation of CPK-MB isoenzyme. The linear cellulose fiber can either be converted to its DEAE (diethyl-amino-ethane) derivative by conventional means on existing filter plugs or a source of DEAE-cellulose can be directly obtained from various vendors and this raw material can be incorporated into cigarette filter tips. A useful cigarette filter tip has been found to have an appropriate configuration (30 mm. long, 10 mm in diameter). The DEAE-filter tip has the following advantages:
1. Low cost and rapid flow matrices.
2. The DEAE-filter tip is readily transported and sold as a disposable cartridge.
3. The DEAE-filter tip column, as a total package, is low cost to be considered as well as disposable.
4. The DEAE-filter tip column or the DEAE-filter tip cartridge can be shipped mailed, stored in dry form reducing inventory space, mailing cost and thus improving storability.

EXAMPLE 5

It is believed important to provide a visual signal for the isolation of the MB fraction of CPK. Slight variations in column bed size, loading capacity, eluting buffers, temperature, and the like all add to slight changes in the elution profile of the MB fraction as obtained from time to time.

It has been found that the addition of green food coloring to Solution #1 provides a suitable marker for marking the MB fraction, and in addition a quite satisfactory quality control for the recycling procedure for re-using the DEAE-dextran column has been devised.

It has been found that conventional green food color is actually composed of a number of chromogens (i.e. blue and yellow). One drop of this green food color concentrate added to one liter or Solution #1 provides just sufficient color for marking purposes on conducting the test. When this green tinted Solution #1 is irrigated through the DEAE-dextran column all of the above pigments (chromogens) are adsorbed at the top of the column. The addition of 1.5 ml of serum onto such a column does not at all displace these three chromogens (green, blue and yellow). Upon further elution of the column with two or three aliquots of green tinted Solution #1, the chromogens continue to adsorb to the upper matrix of the column.

Upon priming the column with 1 ml of Solution #2, the band of chromogens being to descend the column. Upon eluting the column with another 2 ml of Solution #2, a band of the green chromogen elutes off the column together with the CPK-MB fraction. The blue and yellow pigment remain on the column matrices.

Upon the addition of 10-15 ml of Solution #2, the blue chromogen elutes off the column, indicating that the column is ready to be primed with Solution #1, or, as such, is ready for another CPK-MB run. A slight touch of yellow chromogen will continue to accumulate in the column with repeated cycles and this tendency serves to indicate when the column should be discarded, rather than recycled once more. The column will be thoroughly "jaundiced" after about ten (10) recycle steps which is a safe time finally to discard a recycled column.

Since the elution profile of the green chromogen contained in Solution #1 will vary with ionic strength, bed size, loading capacity, and the like, variables coincident to the MB fraction of CPK, this marker serves as a valuable indicator of the overall inventive procedure. In addition, a further advantage is that none of the pigments involved here in any way interferes with the CPK assay using the Rosalki substrate.

The use of green tinted Solution #1 is usable only in the DEAE-dextran columns, or hybrids made of DEAE-dextran with sea sand or inert glass beads. The use of other chromogens may be required for best results using other column matrices. The concept of using a visual marker for CPK-MB, however, that is, using colored indicators should preferably be employed. An alternate modification of this procedure, for example, is to add a drop of diluted green food color to the serum just prior to the transfer of the assayed serum, into the test column.

EXAMPLE 6

This procedure for CPK-MB analysis on fresh human serum has been designed for detecting myocardial infarct (heart attack) as early as one half hour after the initial onset of the attack. Therefore, patients brought to the emergency room or the admission area of a large or a small community hospital may be expeditiously handled by the attending physician for immediate admission or extended observation. Therefore, the acute phase of infarct may be treated, rather than the documentation of an event 6 hours past and medical management may be facilitated by this laboratory datum.

This particular procedure has been tested in a double blind manner on 35 consecutive cases admitted to a special care unit under the direct supervision of a senior attending cardiologist, with the laboratory data performed personally by a full time Director of Clinical Biochemistry over a two month period. An additional 35 cases were also obtained from other in-patients or out-patients of the emergency room service during this period. The laboratory data fully corroborated the final clinical diagnosis and therefore sustains the term "100% sensitivity". In addition, since the invention procedure zeroes in on the slug of MB, a peak, rather than quantitative recovery is made. Thus patients suffering from infarct may be diagnosed as early as one half hour after onset and therefore the acute phase of the infarct can properly be managed by the attending physician.

The expression of CPK-MB is stated as an absolute number (mIu/ml) rather than a percentage of the total CPK activity. This approach is more logical, since the bulk of the CPK activity in the human body is skeletal and contains no MB except in muscle wastage disease. Thus, a patient who has a heart-attack, faints and falls down the stairs, will have a significant MB signal expressed by the invention method way, but an insignificant data when expressed as a percentage of the total.

This kit has been formulated after a full six month service mode of Stat performance 7 days a week, 24 hours a day among three different shifts of technologists and is geared primarily to CPK assays using zero order kinetics.

As a further embodiment of this invention, it has been found possible to use a marker dye for CPK-MB electrophoresis and thereby make a direct and quantitative determination of the MB activity on the visualized segments of the test. It is very valuable to be able to make a quantitative determination of CPK isoenzymes by an electrophoretic method employing a selected marker dye. This visualized segment-CPK-MB and CPK-BB, by virtue of its visibility being aided by the marker dye affords such dissected fractions to be directly assayed for enzymatic activity of CPK by conventional spectrophotometric methods.

The isoenzymes of CPK are clearly separated and identified by cellulose acetate or agarose electrophoresis. The quantitation of three subcomponents (MM, MB, and BB) are usually determined using the Rosalki substrate by either a sandwich or paper overlay technique, with subsequent development of UV-fluorescent spots by maintaining the substrate coated overlay at 37° C. for ½ hour.

Only the relative concentration of the three components can be readily made by fluorometric scanning. The absolute amount of serum CPK-MB content cannot be directly made by this mode of electrophoretic separation.

As has been pointed out above the blue and yellow chromogens found in commercial food colors bind to a human serum protein which co-chromatographs with CPK-MB either in DEAE-dextran column processes or by electrophoretic methods. It has also been found that these food coloring chromogens do not at all affect the Rosalki substrate.

Thus, a new and novel method of directly assaying the CPK-MB or CPK-BB content can be made by cutting out the visualized band after electrophoresis, and thereafter eluting the CPK therein retained and assaying its CPK activity by conventional zero-order kinetic measurements using conventional spectrophotometers. The time saving of this procedure by this new combined electrophoretic enzymatic assay is considerable. The usual time requirement of CPK electrophoresis is approximately one hour, with many cumbersome technical details. The enzymatic electrophoresis or electroenzymatic procedure requires only about fifteen (15) minutes and thus has advantages over the column procedures of the invention.

In certain types of cancer involving the gastrointestinal tract or the genital-urinary tract (cancer of the uterus and prostatic carcinomas), the BB isozyme of CPK is produced voluminously by the malignant cells and such patients, especially in well-advanced stages may present symptoms such as shortness of breath, chest pain and other distressful symptoms. The total serum CPK may be somewhat elevated at admission, and will show a significant MB signal when the column procedure is used. A further confirmatory step is then necessary since the MB signal is presumed to be caused by the enormous amount of CPK-BB present in the serum of such patients (i.e. 80%).

Green food coloring contains two chromogens (blue and yellow) having the respective absorption maxima (625 mu and 410 mu). At a basic pH, 8.0 and above these chromogens migrate anodically, with the yellow moving most rapidly. The blue migrates generally in the region of CPK-BB. When these two chromogens are added to fresh human serum, these chromogens bind tightly with a descrete protein fraction with an electrophoretic mobility essentially identical to CPK-MB. Thus, when an excess of green food color is added to an aliquot of human serum and this preparation is then electrophoresed, three bands are visible (green, blue, and yellow). The blue and yellow bands are the free unbound chromogens. When a limiting amount of green dye is added to serum, only one green band is observed.

If the green band is dissected or otherwise separated from the blue region and each section directly assayed enzymatically for CPK activity, a quick determination can be made as to the source of the MB signal obtained by the hereindescribed procedure. Other refinements of this electroenzymatic procedure, such as automated gel slab dissection using colorimetric sensors, can be employed with this procedure.

The use of green or blue food color as described above for carrying out CPK-electrophoresis is of definitive utility for providing visual assessment of the electrophoretic process during and after completion of an electrophoretic run as well as for sandwich or paper overlays and for fluorometric scanning and positioning.

To summarize:

1. The use of the blue or green food coloring is applicable not only as a marker for CPK-MB by column chromatography as described in this invention but also for electrophoresis.

2. An electrophoretic confirmatory step may be employed on the "MB" fraction by transfering an "MB" eluate into a concentrator (i.e.-Amicon filter cell) and electrophoresing this fraction with added blue or green dye. This confirmation step may be carried out in a conventional manner.

3. A direct electrophoretic assay can be applied utilizing green or blue food coloring. Using an electroenzymatic method, the "MB" fraction described above, or the straight patient serum can be checked by cutting or otherwise isolating the "MB" fraction (green dye section) obtained by electrophoresis and assaying this band directly in a UV spectrophotometer for the Rosalki assay. The dissection of the blue band (free blue chromogen) can also be performed as above for the determination of BB activity. This determination is useful, for example, in assaying the extent and state of certain terminal forms of cancer.

Whereas most column designs are either funnel in shape (i.e. larger in diameter at top, and smaller in diameter toward the bottom) or a straight tubular cylinder. It has been found possible to design a column, which is not only reversible, but contains therein in the middle section, a mixing chamber. One purpose of this mixing chamber is for mixing the matrices of a hybrid matrix, that is a column support made of two different constituencies whose densities are sufficiently distinct so as to allow complete agitation in the mixing chamber by the simple mechanics of multiple hand inversion. For example, in the case of a hybrid matrix such as DEAE-dextran and sea sand, glass beads, and the like the mixture bed can thus be thoroughly agitated prior to its use as a filtration or chromatography column.

The particular column configuration found useful has in addition to the advantage of dispersing hybrid column support matrices (such as DEAE-dextran, sea sand, and the like), a further advantage in that by simply replacing the spigot exit receptacle, the top can become the bottom and vice versa. In addition, such a column can be used with the insertion or attachment of spigots at both ends, thus becoming an effective cartridge in continuous flow filtration or as a chromatographic receptacle.

One primary advantage of such "volumetric design" is that the chromatographic or filtration matrices can be dispersed, uncompacted, and in general conditioned (loosened) to allow rapid flow through such a retentive obstacle.

The reversible column chassis can be polarized (longer at one end, shorter at the other end) or semi-symmetrical. The key feature is that both ends of the column (apertures) are identical so the spigot receptacle can be placed on either end. This added advantage gives considerable flexibility as filtration or chromatography matrices are modified, and by having spigots placed at both ends such a column becomes a cartridge suitable for continuous flow closed systems.

Thus a bellows or a volumetric shaped column chassis is believed to be unique in chromatographic column design since such a column would appear to have no facilitative advantage or adequate resolving power. This unique design is effective because only the ends of the column are used for chromatographic resolution; the widened main chassis of the column is used primarily for mixing the hybrid chromatographic matrices (i.e. DEAE-dextran sea sand, and the like). This column design is especially engineered as a device for separating the CPK-MB iso-enzyme as part of the expendible supply of a heart attack diagnostic kit.

Another embodiment of the invention for preferred column design as well as a "packaged kit" is described as follows.

Column matrices composed of DEAE-dextran such as Sephadex A50 are extremely gelatinous, almost "mucoid" in nature. Although their exchange characteristics are exceptionally desireable, their flow rates are generally quite slow. This problem has been solved by a column spigot design consisting of a cigarette filter tip which is shielded by a layer of sea sand or inert glass beads.

The conventional laboratory test tube, as used in the hospital or in a physicians office, is the "Vacutainer" type tube 16>100 mm. Another device frequently used in larger routine hospital laboratories is a serum separator which contains a rubber-type septum or collar containing a porous disc on a plastic cylinder to be inserted into the 16×100 mm. tube.

The novel design, which incorporates all of the above, and by modifying the septum—makes the serum separator instead, into a column. The modified column loaded with the appropriate bed volume of DEAE-dextran, therefore may be packaged directly in the 16×100 mm. tube with appropriate cap—which will cover both the inserted column as well as the recipient 16×100 mm. tube.

Although the tube dimensions described above are not absolute, the above description illustrates the column invention concept developed from existing laboratory paraphernalia.

The spigot septum should have slits or vents for free movement of air or liquid, so that the purpose of the septum is to house the cigarette filter tip plug as a spigot, and additionally, to serve as an anchor into the recipient tube. Thus, after removing the top enclosure cap, by lifting the 10×100 mm. glass or clear plastic cylinder, the column is ready to receive the patient serum for processing the CK-MB serum sample. The column will be lifted to the top rim of the recipient column so that maximal eluate space will be provided by the 16×100 recipient tube. Since the 16×100 tube can hold 14 ml. of fluid, the addition of 1.5 ml. of serum, plus 2×4 ml. of solution #1 (8 ml.) plus 1 ml. (prime) of Solution #2—will result in the collection of approximately 10 ml. of eluate for discard purposes.

For purposes of collecting the 2 ml. of the CK-MB fraction, the column is removed from the first recipient package tube, to another recipient tube, and 2 ml. of Solution #2 are now added to the column.

Operating in this manner, specimen identification can be maintained with minimal possibility of error. The use of conventional tube racks or tube blocks (platforms) would suffice for the entire collection process.

The packaging concept is considerably simplified by the following considerations.

a. Since these columns are completely encased in the 16×100 mm. recipient tube and overhead enclosure cap, the packed columns do not require residual column buffer as a supernate. Approximately 1 ml. of Solution #1 buffer is stored in the bottom of recipient tube. This allows the porous cigarette filter tip in the spigot aperture to be thoroughly immersed in the fluid.

b. In effect, the column is immersed in the buffer reservoir and the column matrices itself is a hydrated gel. Thus, when these columns are stored on their sides, as in a box in transit or in storage—the column matrix top (meniscus) will not be slanted or distorted, since the columns were poured and packed, drained of excess buffer—so that the bed/gel meniscus is perfectly flat. These wet/dry column beds, however, will not crack because of the excess moisture provided by the 1 ml. of buffer in the recipient reservoir which functions as a wick.

c. Since all columns will have a "perfectly" horizontal top bed meniscus—problems of occasional channeling during serum processing are substantially or entirely eliminated.

d. Since the column/recipient tube capped would be seal-tight and compact, these items can be packaged and stored just like expendible Vacutainer tubes in cartons of 100 columns per package.

The concept of priming on a DEAE-dextraon column has not previously been possible because of the possibility of channeling, and other mechanical problems. The use of tartrazine yellow/brilliant blue #1 (the green food color) along with serum proteins allows a predictable priming step for such column.

It has been found that fast flow rate DEAE-dextran matrices can be prepared by conditioning the matrix with human or bovine albumin. This type of protein overcoating effect which speeds the flow rate without distorting the elution profile or resolution of CK-MB has particularly been noticed using recycled columns as described herein.

In a hospital study of tests for serum total CK and serum CK and MB, certain other biological data has been developed.

A large spectrum of disease states are correlated with an above normal serum CK-MB. These include such conditions as septicemia, perotinitis, necrotic liver, shock from major superficial burns, drug sensitivity, etc. All of these conditions as well as myocardial infarct and myocarditis are serious medical conditions. Other conditions which give a CK-MB signal—but is due to CK-BB partially carried over into the MB peak-slug, are cancer of the prostate, stomach, intestine or postpartum (uterine contractions, etc.)

Many older patients, especially aged females of small stature, have unremarkable total serum CK values even after an infarct. The patients also include subjects with multiple previous infarcts, advanced coronary artery disease, and generalized cardiac myopathy.

This data base was accumulated because of the application of the hereindescribed procedure on patient sera at or above the high normal range (i.e.—100 U/L, normal range=0-110 U/L). Although the intent was to detect infarcts as early as 45 minutes post theoretical zero time (other techniques are suitable only after 4-5 hours post theoretical zero time), the work load requirements for detecting approximately seven clinically valid infarcts per week require the use of 100-150 columns per week. Accordingly, the monthly inventory needs are easily 700-1000 columns requiring packaging, storage and disposability. As and when more aggressive intravenous modes of immediate treatment of both septicemia and infarcts become available, the work load/inventory requirements may expand easily by a factor of 2 or 3, due to more repetitive sampling (blood specimens) of the same patient for time sequential studies.

Thus, the columns, are best presented if they can be handled as a self-contained thoroughly disposable item—similar to Vacutainer tubes. It is further desirable if no racks were required as such devices are generally cumbersome, space occupying and rather costly. It is also helpful if such columns can be used as preparative devices for other analytical work, including high pressure liquid chromatography.

It has further been discovered by repetitive assays and recovery experiments on the column isolation procedure of CPK-MB reveal that 70 percent of the total MB fraction is recovered in the 2.0 ml eluate. Since only 1.5 ml of serum is applied on a 2.0 ml. bed DEADE-dextran column and a 2.0 ml. slug is collected for the MB fraction, of which only 70% is recovered (since the prime step fore-shoulder, and the MB after-shoulder are not recovered in the 2.0 ml. MB peak slug)—the correct calculation for total CPK-MB should be:

| Total CPK-MB fraction | |
|---|---|
| in serum | $= \text{MB signal} \times \frac{2.0 \text{ ml}}{1.5 \text{ ml}} \times \frac{100\%}{70\%}$ |
| | $= \text{MB signal} \times \frac{4}{3} \times \frac{10}{7}$ |
| | $= \text{MB signal} \times \frac{40}{21}$ |
| | $= \text{MB signal} \times 2$ |

Thus, the absolute signal for example obtained in the 2.0 ml. MB slug should really be multiplied times two ($\times 2$) in order to obtain the CPK-MB in fresh human serum.

Using for instance, the Beckman TR enzyme Analyzer, the MB values were empirically deduced as:

<3 IU/L—negative
3 IU/L—questionable
>3 IU/L—positive

The reason for this arbitrary cut-off was primarily due to "electrical" noise on the TR of 2 IU/L. After a year's experience in the 24 hour per day STAT service mode (450) consecutive days), and after a development of an exhaustive wash cycle protocol for removing microbial contaminants from the TR plumbing—it appears that the revised MB values should be:

<3 IU/L=negative
3 IU/L=questionable
>3 IU/L=positive

These new values, when derived on the TR—should only be on repetitive assays of such weak MB samples such as triplicates or quadruplicates. Speed of replicate assays are readily facilitated on the TR using a lag-free CPK substrate (i.e. Boehringer CK-NAC, etc.) using the LDH mode which is only a one minute chemistry.

All of the TR CPK values may be reproduced from sample to sample using the same substrate for CPK (provided that that substrate is adequate for the TR analyzer) on any programmable 37° C., 340 UV spectrophotometer (Gilford 300-N, Beckman 25, etc.). Problems of microbial effects become minimized due to short plumbing, (sipper system, etc.), or curvettes. Since the TR sample to substrate ratio is 0.05 ml/0.5 ml (0.1 ml sample/1.0 ml substrate)—this same proportion is observed for reproducing TR CPK values. Using a "lag-free" substrate the $\Delta O.D.^{340}$ obtained at the timed interval 40 second-100 second gives a $\Delta O.D.^{340}$ synonymous with mIU/ml. Where substrate lag is observed (Beckman, etc.)—the time interval would be 5 minutes-6 minutes.

To eliminate the need to multiply the TR-MB values by two ($\times 2$) or on any other enzyme analyzer, for that matter—the sample to substrate ratio should be: 0.2 ml sample/0.8 ml substrate. The $\Delta O.D.^{340}$ values here obtained will be twice the value of the (0.1 ml/1.0 ml) specimens previously described. At low MB levels, this adjustment will be exactly twice the signal and no multiplication ($\times 2$) becomes necessary.

Enzyme analyses for total CPK and CPK-MB must be carefully worked out and defined depending on instrumentation and also substrate formulations. Provided that the enzymatic determinations are linear (follow "Beers" law)—the use of the qualitative column approach for quantitating CPK-MB either by a mechanical multiplication factor of 2 ($\times 2$) or more preferably, the sample/substrate ratio should be changed from 0.1 ml/1.0 ml to 0.2 ml/0.8 ml. Alternatively on some instrumentations such as the Beckman TR, etc.,—the calibration knob can be doubled (i.e.—520→1040). These conditions on the Beckman TR is allowed by incorporating a sample splitter (i.e. Technicon part PT-10, etc.) so that both sample pumps are operating. Thus the sample to substrate ratio has been altered from 0.05 ml/0.5 ml to 0.10 ml sample/0.5 ml substrate.

A preferred invention procedure for isolating a consistent portion of CK-MB has generally been found to be 70% of theoretical.

Since 1.5 ml of serum is added to the column, and 2.0 ml of Solution #2 is collected, the overall dilution of CK-MB activity is:

$$= \frac{70}{100} \times \frac{1.5}{2.0}$$

$$= \frac{210}{400}$$

$$= \frac{1}{2}$$

Thus the activity of CK-MB recovered and assayed in the 2 ml cup, must be multiplied ×2.

This is effectively performed by the following:

Total serum CK=0.1 ml unknown+0.9 ml substrate
CK-MB=0.2 ml unknown+0.8 ml substrate In a manual type spectrophotometer with a suitable 37° C. jacketed cuvette, the ΔO.D. of 100 seconds will provide the true enzyme activity of both the total serum CK as well as the total serum CK-MB.

In automated instruments which have a fixed unknown to substrate volume ratio, the CK-MB value can be obtained either by multiplying the MB value ×2 or by changing the calibration knob (amplifier) ×2.

Preferably the kit design should incorporate 0.1 ml serum+0.9 ml substrate for total CK, 0.2 ml "MB eluate"+0.8 ml substrate for MB, as the tested methodology and the 100 second 340 O.D. reading is synonymous with M±u/ml (U/L).

The ratio of 0.1 ml unknown/0.9 ml substrate vs 0.2 ml unknown MB/0.8 ml substrate is extremely important not only for the above but because these are volumes which are readily pipittable with accuracy, are readily aspirated into a sipper cuvette (1 ml), but most importantly the 0.2 ml of Solution #2 salt added to 0.8 ml of substrate, does not cause any enzyme inhibition which higher salt mixtures would effect. Thus the true MB values can be reported and probably explains the extremely high sensitivity of the herein disclosed method.

Because of this sensitivity, for reasons stated above, the CK-MB signal is detected within 45 minutes to 60 minutes past zero time from infarct, or infarct on extremely aged patients whose cellular enzyme levels are quite low, and finally, but most importantly in patient suffering from septicemia (bactermia), perotinitis, necrotic liver, shock, etc. Electrophoretic methods do not detect infarct until 5-6 hours past zero time and they do not pick up septicemia at all.

These latter conditions, other than infarct, generally do not peak—but generally show a flat effect versus time, sequentially. Septicemia has been found by this technique to be rather common and a definitive diagnosis helped by this type of laboratory data facilitates immediate intravenous antibiotic therapy which can be initiated considerably ahead of microbial culture identification.

In some patients in a debilitated state—such as a patient with advanced cancer undergoing radiation treatment—confirmation of the CK-MB signal will be required since the signal may be due to CK-BB (Ca of the stomach, bladder, or prostate)—or it may be the result of bacteremia caused by the weakened resistance of the body from radiation or chemotherapy. In such case, the 2 ml fraction of the "MB" eluate may be concentrated readily in a concentrating cell and using electrophoresis.

Application of the Green Food Marker dye is extremely useful for purposes of identifying the different bands of CK-isozymes, MM, MB and BB. Thus the use of the green food marker for electrophoretic as well as column separation of CK-isozymes are apparent. The electrophoretic buffer should however be Tris/aspartate or Tris/maleate, etc. rather than Tris/Barbital (Veronal) since the alkaloid competes for the same binding sites on the alpha-2 globulin as does the brilliant blue #1 and tartrazine yellow (green food color).

This combined column followed by electrophoretic analysis of the concentrated "MB" cut has decided advantages over antibody inhibition or Radio Immuno Assay procedures which cannot distinguish between CK-MB and CK-BB. This confirmation of the "MB cut" obtained by this column procedure is made possible by electrophoretic analysis—since the "MB cut" is essentially "protein free" allowing rapid concentration by dry dialysis techniques (Amicon filters, etc.) or by centrifugation through molecular sieves.

A variety of pathological states can be detected by the method described above and beyond myocarditis infarct, drug overdose, and the like. In fact, the detection of infarcts by this method in extremely aged patients is of special value.

The usefulness of this MB data for septicemia, however, seems fairly obvious—as this condition can affect young, otherwise viable patients. Management of early detected septicemia can readily be instituted by antibiotics and other indicated drugs.

A technique has been discovered for unifying the International Enzyme Unit of Activity optical density and this method is described below.

A number of enzyme or chemical assays employing rate reactions of zero order nature—quantify the level of enzyme activity or another component (glucose, BUN,) using coupled enzyme systems where one of the products liberated is DPNH (NADH). The utility of using DPNH as a signal for quantification is its extremely high extinction or absorbency at 340 mu. This type of UV chemistry is extremely popular in chemical laboratories because of both its precision and sensitivity.

The molar extinction of DPNH at 340 mu for a 1 cm light path is $6.22 \times 10^3$.

The millimolar extinction is 6.22

The micromolar extinction is 0.006 or 1 muM/ml—0.006

Thus it follows that in a 1 ml system 1 muM of product generated would give an optical density at 340 mu of 0.006 in 60 seconds.

The Enzyme Unit is defined as the turnover of 1 uM substrate in 60 seconds under standard conditions (37° C., etc.).

1 Unit≅1 u Mole S→P/60 sec
or 1 m u≅m u M S→P/60 sec
Since: 1 uM/ml DPHN=6.22 O.D. 340
1 mUM/ml DPNH=0.006
1 m U=ΔO.D.$^{340}$/60 sec=0.006
1 m U=ΔO.D.$^{340}$/100 sec=0.010
0.1 m U=ΔO.D.$^{340}$/100 sec=0.001

If: 0.1 ml of unknown + 0.9 ml of substrate O.D. 340

$\frac{37° C.}{100 \text{ sec}}$ ⟶ 0.001 O.D. 340/100 sec

Then: 0.001 = 1 mIU/ml of the unknown

If the O.D. of 0.006 is called 6 units of signal, it follows that 10 units of signal/100 sec. will equal 1 mI Unit/ml, since by definition:

1 Unit of Enzyme Activity = 1 u mole product/60 sec
where 1 milli I unit = 1 milli u M If 1 milli Unit of E activity generates 10 units of signal/100 sec, it follows that 0.1 milli Unit $\cong 0.001^{O.D.\ 340}$ in a 1 ml system.

Therefore if 0.1 ml of unknown and 0.9 ml of substrate were allowed to react at 37° C., the $\Delta$O.D. of 100 seconds of 0.001 would be equal to 1 mIu/ml of the unknown.

In this manner the O.D. readings and the enzyme or chemical measurement will be synonymous.

What is claimed is:

1. A process for identification and collection of the creatine phosphokinase-MB fraction from human blood serum, which comprises the steps of priming a chromatographic column having a packing consisting essentially of DEAE-dextran with a strongly anionic polymer as conditioner, introducing a green food marker dye, introducing a sample of human blood serum from a human patient into the primed column, permitting the absorbed fraction from said serum to move from the top of the column matrices through the column to the bottom of the column matrices, introducing about 1 ml. of a solution of 0.3 M NaCl and 0.05 M "Tris" at a pH of 6.9 and identifying by visual observation of the marker dye and collecting from the bottom of said column about 70% of the creatine phosphokinase-MB fraction present in said sample at 100% predictability and in concentrated form.

2. The process of claim 1 in which an electrophoresis step is incorporated and the green food marker dye is employed with said sample of human blood serum during introduction into said column, thereby facilitating visual observation and separation of creatine phosphokinase isoenzyme during said electrophoresis step.

3. The process of claim 1 in which the absolute amount of creatine phosphokinase-MB is measured and the value thus obtained is used for detection of septicemia in said patient.

4. The process of claim 1 in which alpha-2 globulin and a covalently linked chromagen attached thereto is introduced into said primed column, thereby serving as a marker for convenient location of the creatine phosphokinase-MB fraction in the column.

5. The process of claim 1 in which said anionic polymer is albumin.

* * * * *